United States Patent
Ohno et al.

(10) Patent No.: US 7,208,644 B2
(45) Date of Patent: Apr. 24, 2007

(54) PRODUCTION AND USE OF HEXAFLUOROETHANE

(75) Inventors: Hiromoto Ohno, Kawasaki (JP); Toshio Ohi, Tokyo (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 11/028,154

(22) Filed: Jan. 4, 2005

(65) Prior Publication Data

US 2005/0159632 A1    Jul. 21, 2005

Related U.S. Application Data

(62) Division of application No. 10/398,441, filed as application No. PCT/JP02/08034 on Aug. 6, 2002, now Pat. No. 7,045,668.

(60) Provisional application No. 60/314,309, filed on Aug. 24, 2001, provisional application No. 60/314,310, filed on Aug. 24, 2001.

(30) Foreign Application Priority Data

Aug. 6, 2001    (JP) ............................ 2001-238012
Aug. 16, 2001    (JP) ............................ 2001-247380

(51) Int. Cl.
*C07C 17/383*    (2006.01)
*C07C 17/38*    (2006.01)

(52) U.S. Cl. .................. 570/123; 570/177; 570/178

(58) Field of Classification Search ................ 570/134, 570/177, 178, 123
See application file for complete search history.

(56) References Cited

U.S. PATENT DOCUMENTS

| | | | |
|---|---|---|---|
| 4,748,285 A | 5/1988 | Foulletier | |
| 5,453,551 A | 9/1995 | Lacroix et al. | |
| 5,523,499 A | 6/1996 | Corbin et al. | |
| 5,710,351 A | 1/1998 | Ohno et al. | |
| 6,340,781 B1 * | 1/2002 | Shields et al. | ............. 570/177 |

FOREIGN PATENT DOCUMENTS

JP    7324044 A    *    12/1995

OTHER PUBLICATIONS

Databse WPI, Section Ch, Week 199749, Derwent Publications Ltd., London, GB, Class E16, AN 1997-532712, XP002222632 & JP 09 255596 A (Showa Denko KK), Sep. 30, 1997 abstract.
XP-001120714, COQ, et al. "Conversion under hydrogen of dichlorodifluoromethane over bimetallic palladium catalysts" Applied Catalysis, A: General, vol. 101, 1993, pp. 41-50.
International Search Report, for PCT/JP02/08034, dated Nov. 27, 2002.

* cited by examiner

*Primary Examiner*—Rosalynd Keys
(74) *Attorney, Agent, or Firm*—Sughrue Mion, PLLC

(57) ABSTRACT

A process for production of high-purity hexafluoroethane, wherein a mixed gas containing hexafluoroethane and chlorotrifluoromethane is reacted with hydrogen fluoride in a gas phase in the presence of a fluorination catalyst at 200–450° C., for fluorination of the chlorotrifluoromethane, or wherein pentafluoroethane containing chlorine compounds with 1–3 carbon atoms is reacted with hydrogen in a gas phase in the presence of a hydrogenation catalyst at 150–400° C., and the product is then reacted with fluorine in a gas phase in the presence of a diluent gas.

16 Claims, No Drawings

PRODUCTION AND USE OF HEXAFLUOROETHANE

CROSS REFERENCE TO RELATED APPLICATIONS

This is a divisional application of U.S. application Ser. No. 10/398,441 filed Apr. 4, 2003, now U.S. Pat. No. 7,045,668, which is a national stage application of PCT Application No. PCT/JP02/08034 filed Aug. 6, 2002, which claims benefit from U.S. Provisional Application No. 60/314,309 filed Aug. 24, 2001 and U.S. Provisional application No. 60/314,310 filed Aug. 24, 2001, the disclosure of all of which is incorporated herein by reference.

TECHNICAL FIELD

The present invention relates to production and use of hexafluoroethane.

BACKGROUND ART

Hexafluoroethane ($CF_3CF_3$) is used, for example, as a cleaning gas or etching gas for semiconductors. Several processes have conventionally been known for the production of $CF_3CF_3$, such as (1) electrolytic fluorination processes using ethane and/or ethylene as the starting material, (2) thermal decomposition processes involving thermal decomposition of tetrafluoroethylene, (3) processes in which acetylene, ethylene and/or ethane are fluorinated using metal fluorides, (4) processes in which dichlorotetrafluoroethane or chloropentafluoroethane is fluorinated using hydrogen fluoride in the presence of a fluorination catalyst, and (5) direct fluorination processes involving reaction of tetrafluoroethane and/or pentafluoroethane with fluorine.

However, when the process of (4) above is used, for example, the resulting $CF_3CF_3$ contains impurities in the form of compounds derived from the starting material or compounds newly produced by the reaction. Particularly problematic among such impurities are chlorine compounds, which are difficult to separate from $CF_3CF_3$.

When the process of (5) above is used, for example, the resulting $CF_3CF_3$ also contains impurities in the form of compounds derived from the starting material or compounds newly produced by the reaction. These impurities also include chlorine compounds which are difficult to separate from $CF_3CF_3$. Purification may be carried out before reaction with fluorine gas in order to reduce the chlorine compounds in the starting material, but industrial application of conventionally known purification processes is difficult in most cases.

The chlorine compounds in $CF_3CF_3$ include compounds such as chloromethane, chlorodifluoromethane, chlorotrifluoromethane, chloropentafluoroethane, dichlorotetrafluoroethane, chlorotetrafluoroethane, chlorotrifluoroethane, chlorotrifluoroethylene and the like.

Among these chlorine compounds, chlorotrifluoromethane is difficult to separate because it forms an azeotropic mixture with $CF_3CF_3$. Examples of methods of purifying $CF_3CF_3$ containing chlorotrifluoromethane include the method described in U.S. Pat. No. 5,523,499 in which $CF_3CF_3$ containing impurities such as trifluoromethane ($CHF_3$) and chlorotrifluoromethane ($CClF_3$) is contacted with an adsorbing agent such as active carbon or a molecular sieve to adsorb and remove the impurities.

Purification methods using such adsorbing agents require special equipment for regeneration of the adsorbing agents at roughly consistent intervals in the case of constant operation, although this depends on the impurity content. For example, in a process wherein two adsorption towers are provided and operation alternately switches between a step of adsorption of impurities and a step of regeneration of the adsorbing agent, large amounts of gas may be continuously treated, but the adsorbed and removed chlorotrifluoromethane cannot be directly released into the atmosphere since it is a specific freon implicated in destruction of the ozone layer, and therefore some means must be used to render it harmless.

On the other hand, pentafluoroethane ($CF_3CHF_2$) is used, for example, as a low-temperature refrigerant, or as a starting material for production of hexafluoroethane ($CF_3CF_3$). As examples of conventionally known processes for production of pentafluoroethane there may be mentioned the following:

(1) a process in which perchloroethylene ($CCl_2=CCl_2$) or its fluorinated product is fluorinated with hydrogen fluoride (Japanese Unexamined Patent Publication No. 8-268932, Japanese Unexamined Patent Publication No. 9-511515), (2) a process in which chloropentafluoroethane ($CClF_2CF_3$) is subjected to hydrogenolysis (Japanese Patent No. 2540409), and (3) a process in which fluorine gas is reacted with halogen-containing ethylene (Japanese Unexamined Patent Publication No. 1-38034).

When such processes are used, the major impurities in the target product, pentafluoroethane, are chlorine compounds which of course contain chlorine atoms in the molecules. Examples of such chlorine compounds include compounds with one carbon atom such as chloromethane, chlorodifluoromethane and chlorotrifluoromethane, compounds with two carbon atoms such as chloropentafluoroethane, dichlorotetrafluoroethane, chlorotetrafluoroethane and chlorotrifluoroethane, and unsaturated compounds such as chlorotrifluoroethylene.

When hexafluoroethane is produced by direct fluorination reaction with pentafluoroethane and fluorine gas ($F_2$), any of these chlorine compounds included in the pentafluoroethane will react with the fluorine gas, producing chlorine, hydrogen chloride, chlorine fluorides, or various chlorofluorocarbons. While perfluorocarbons (PFCs) included in the pentafluoroethane do not present any notable problem, chloromethane ($CH_3Cl$) and chlorodifluoromethane ($CHClF_2$) will react with fluorine gas to produce chlorotrifluoromethane ($CClF_3$). Hexafluoroethane and chlorotrifluoromethane form an azeotropic mixture, and therefore removal of chlorotrifluoromethane is difficult even by distillation or adsorption purification. Thus, when pentafluoroethane and fluorine gas are reacted to produce hexafluoroethane, it is preferred to use pentafluoroethane with a minimal chlorine compound content.

With conventional processes for production of pentafluoroethane, the chlorine compound content in the pentafluoroethane can be as high as about 1 vol % in total. Repeated distillation has therefore been considered to remove the chlorine compounds in the pentafluoroethane and thus increase its purity, but because of the increased production cost of the distillation, as well as distillation loss, this procedure has been uneconomical, while some of the chlorine compounds also form azeotropic mixtures or azeotrope-like mixtures with pentafluoroethane and create a situation in which it very difficult to separate the chlorine compounds by distillation procedures alone. In particular, chloropentafluoroethane ($CClF_2CF_3$) is usually included in pentafluoroethane at a concentration of a few thousand ppm or greater, but since pentafluoroethane and chloropentafluoroethane form an azeotropic mixture, they are difficult to separate by distillation, which is the commonly employed separation and purification method.

DISCLOSURE OF THE INVENTION

It is an object of the present invention, which was accomplished under the conditions described above, to provide an industrially advantageous process for production of high-purity hexafluoroethane, which can be used as an etching gas or cleaning gas for semiconductor device manufacturing steps, as well as the use of high-purity hexafluoroethane obtained by the process.

As a result of diligent research in light of the circumstances of the prior art as described above, the present inventors have completed the present invention upon finding that the above-mentioned problems can be solved by employing a step in which a mixed gas containing hexafluoroethane and chlorotrifluoromethane is reacted with hydrogen fluoride in a gas phase in the presence of a fluorination catalyst and at a prescribed temperature, for fluorination of the chlorotrifluoromethane.

The invention therefore provides a process for production of hexafluoroethane which comprises a step in which a mixed gas containing hexafluoroethane and chlorotrifluoromethane is reacted with hydrogen fluoride in a gas phase in the presence of a fluorination catalyst at 200–450° C., for fluorination of the chlorotrifluoromethane.

The invention further provides a process for production of hexafluoroethane comprising the following steps (1) and (2):

(1) A step in which a mixed gas containing hexafluoroethane and chlorotrifluoromethane is reacted with hydrogen fluoride in a gas phase in the presence of a fluorination catalyst at 200–450° C. to fluorinate the chlorotrifluoromethane to convert it to tetrafluoromethane.

(2) A step in which the mixed gas containing hexafluoroethane and tetrafluoromethane obtained in step (1) is distilled to obtain purified hexafluoroethane.

The invention still further provides a hexafluoroethane product containing hexafluoroethane at a purity of 99.9997 vol % or greater, obtained using the aforementioned process.

The invention still further provides an etching gas containing the aforementioned hexafluoroethane product.

The invention still further provides a cleaning gas containing the aforementioned hexafluoroethane product.

As a result of more detailed investigation, the present inventors have achieved completed the present invention upon finding that the above-mentioned problems can also be solved by employing a production process comprising a step (1) in which pentafluoroethane containing chlorine compounds with 1–3 carbon atoms is reacted with hydrogen in a gas phase in the presence of a hydrogenation catalyst at a prescribed temperature, for hydrogenation of the chlorine compounds, and a step (2) in which the product of step (1) is reacted with fluorine in a gas phase in the presence of a diluent gas to produce hexafluoroethane.

The invention therefore provides a process for production of hexafluoroethane which comprises a step (1) in which pentafluoroethane containing chlorine compounds with 1–3 carbon atoms is reacted with hydrogen in a gas phase in the presence of a hydrogenation catalyst at 150–400° C., for hydrogenation of the chlorine compounds, and a step (2) in which the product of step (1) is reacted with fluorine in a gas phase in the presence of a diluent gas to produce hexafluoroethane.

The invention further provides a hexafluoroethane product containing hexafluoroethane at a purity of 99.9997 vol % or greater, obtained using the aforementioned process.

The invention still further provides an etching gas containing the aforementioned hexafluoroethane product.

The invention still further provides a cleaning gas containing the aforementioned hexafluoroethane product.

BEST MODE FOR CARRYING OUT THE INVENTION

A hexafluoroethane production process according to a first aspect of the invention will now be explained in detail.

As mentioned above, various processes are conventionally known for production of hexafluoroethane. As industrially safe and economical processes there may be mentioned the following:

(1) processes in which dichlorotetrafluoroethane or chloropentafluoroethane is fluorinated using hydrogen fluoride in the presence of a fluorination catalyst;

(2) processes involving reaction of tetrafluoroethane and/or pentafluoroethane with fluorine gas.

In these processes (1) and (2), compounds such as dichlorotetrafluoroethane, chloropentafluoroethane or pentafluoroethane which are used as the starting materials can be produced using, for example, tetrachloroethylene ($CCl_2=CCl_2$) as the starting material, while compounds such as tetrafluoroethane can be produced using trichloroethylene ($CHCl=CCl_2$) as the starting material. Regardless of the method used, however, the resulting hexafluoroethane contains starting material-derived chlorine compounds as impurities, and the content of impurities tends to increase at a higher reaction temperature.

For example, pentafluoroethane ($CF_3CHF_2$), which is commercially available as a refrigerant, contains these chlorine compounds as impurities. When chlorine compound-containing pentafluoroethane and fluorine gas are directly reacted for fluorination to produce $CF_3CF_3$, reaction between the chlorine compounds in the pentafluoroethane and the fluorine gas produces, among other compounds, chlorine, hydrogen chloride, chlorine fluorides, and various chlorofluorocarbons. For example, chlorodifluoromethane included as an impurity reacts with fluorine gas to produce chlorotrifluoromethane. The chlorotrifluoromethane forms an azeotropic mixture with $CF_3CF_3$, and is therefore a very difficult compound to separate, even by distillation.

The hexafluoroethane production process according to the first aspect of the invention comprises a step in which a mixed gas containing chlorotrifluoromethane and hexafluoroethane, which are extremely difficult to separate, is reacted with hydrogen fluoride in a gas phase in the presence of a fluorination catalyst at 200–450° C., for fluorination of the chlorotrifluoromethane. The mixed gas contains hexafluoroethane at 99.9 vol % or greater, while also containing chlorotrifluoromethane as an impurity.

The fluorination catalyst used in this process is preferably a catalyst with trivalent chromium oxide as the major component, and contains nickel, zinc, indium and/or gallium in an atomic ratio of 0.01–0.6 with respect to chromium. The catalyst may be in the form of a supported catalyst or a bulk catalyst, and when it is in the form of a supported catalyst, the carrier is preferably active carbon, alumina, partially fluorinated alumina or the like, with a component-supporting rate of preferably no greater than 30 wt %.

The temperature for the reaction between the hydrogen fluoride and the mixed gas containing hexafluoroethane and chlorotrifluoromethane in the presence of the fluorination catalyst is 200–450° C., and preferably 250–400° C. If the reaction temperature is below 200° C., the chlorotrifluoromethane is not readily fluorinated, and if the reaction temperature is above 450° C. the catalyst life is shortened, and the impurities will tend to increase.

In the fluorination reaction, the molar ratio of the hydrogen fluoride and the mixed gas (hydrogen fluoride/mixed gas containing hexafluoroethane and chlorotrifluoromethane) is preferably in the range of 0.05–10, and more preferably in the range of 0.05–5. If the molar ratio of the hydrogen fluoride and the mixed gas is smaller than 0.05, various chlorofluorocarbons will tend to be readily produced by side-reactions, and if it is greater than 10, an economically disadvantageous situation will result, such as increased reactor size and recovery of unreacted hydrogen fluoride.

The concentration of the chlorotrifluoromethane in the mixed gas is preferably no greater than 0.1 vol % and more preferably no greater than 0.05 vol % of the mixed gas.

The mixed gas is preferably obtained by reacting dichlorotetrafluoroethane and/or chloropentafluoroethane with hydrogen fluoride in a gas phase in the presence of a fluorination catalyst. Alternatively, the mixed gas may be obtained by reaction of tetrafluoroethane and/or pentafluoroethane with fluorine gas.

The process for production of hexafluoroethane according to the first aspect of the invention may comprise the following steps (1) and (2).

(1) A step in which a mixed gas containing hexafluoroethane and chlorotrifluoromethane is reacted with hydrogen fluoride in a gas phase in the presence of a fluorination catalyst at 200–450° C. to fluorinate the chlorotrifluoromethane and convert it to tetrafluoromethane.

(2) A step in which the mixed gas containing hexafluoroethane and tetrafluoromethane obtained in step (1) is distilled to obtain purified hexafluoroethane.

The chlorotrifluoromethane reacts with hydrogen fluoride in the presence of a fluorination catalyst to produce tetrafluoromethane ($CF_4$), as shown in the following formula (1).

$$CClF_3 + HF \rightarrow CF_4 + HCl \qquad (1)$$

Instead of reaction of the hexafluoroethane, the chlorotrifluoromethane impurity reacts with the hydrogen fluoride. Since the difference in boiling points between the resulting $CF_4$ and the unreacted residual $CF_3CF_3$ is about 50° C., and the $CF_4$ and $CF_3CF_3$ therefore do not form an azeotropic mixture, they can be easily separated by any known distillation procedure.

The fluorination catalyst of step (1) is preferably a supported catalyst or a bulk catalyst with trivalent chromium oxide as the main component.

In step (1), the molar ratio of the hydrogen fluoride gas and mixed gas (hydrogen fluoride/mixed gas containing hexafluoroethane and chlorotrifluoromethane) is preferably in the range of 0.05–10, and the concentration of the chlorotrifluoromethane in the mixed gas of step (1) is preferably no greater than 0.1 vol %.

The mixed gas of step (1) is preferably obtained by reacting dichlorotetrafluoroethane and/or chloropentafluoroethane with hydrogen fluoride in a gas phase in the presence of a fluorination catalyst. Alternatively, the mixed gas of step (1) may be obtained by reaction of tetrafluoroethane and/or pentafluoroethane with fluorine gas.

The method of removing the acid component consisting of the hydrochloric acid produced by the reaction of formula (1) and the excess hydrogen fluoride may be, for example, a method of contacting with a purifying agent or a method of contacting with water or an aqueous alkali solution. The gas composed mainly of $CF_3CF_3$ after the acid component has been removed may be dehydrated using a dehydrating agent such as zeolite and subjected to a distillation, procedure to cut the low boiling point fraction, in order to obtain high-purity $CF_3CF_3$.

A hexafluoroethane production process according to a second aspect of the invention will now be explained in detail.

This process is a process for production of hexafluoroethane which comprises a step (1) in which pentafluoroethane containing chlorine compounds with 1–3 carbon atoms is reacted with hydrogen in a gas phase in the presence of a hydrogenation catalyst at 150–400° C., for hydrogenation of the chlorine compounds, and a step (2) in which the product of step (1) is reacted with fluorine in a gas phase in the presence of a diluent gas to produce hexafluoroethane.

As mentioned above, the pentafluoroethane used for this process is usually produced by fluorination of perchloroethylene ($CCl_2=CCl_2$) or its fluorinated product with hydrogen fluoride (HF), and the pentafluoroethane will contain, as starting material-derived chlorine compounds, chloromethane, chlorodifluoromethane, chloropentafluoroethane, dichlorotetrafluoroethane, chlorotetrafluoroethane, chlorotrifluoroethane, chlorotrifluoroethylene and the like. A known distillation procedure may be employed for high purification of the pentafluoroethane containing these compounds, but because the chlorine compounds and pentafluoroethane form azeotropic mixtures or azeotrope-like mixtures, their separation and purification is extremely difficult, requiring an increased number of distillation steps and distillation towers and thereby creating a problem, in economic terms, due to the added equipment and energy costs.

This process begins with step (1) in which the chlorine compounds containing chlorine atoms and included as impurities in the pentafluoroethane are first reacted with hydrogen in a gas phase in the presence of a hydrogenation catalyst at 150–400° C. for hydrogenation, to convert them to hydrofluorocarbons (HFCs) and the like. For example, using hydrogen for hydrogenation of the chloropentafluoroethane ($CF_3CClF_2$) and chlorotetrafluoroethane ($CF_3CHClF$) included as impurities in the pentafluoroethane takes place the reactions represented by formulas (2) and (3) below.

$$CF_3CClF_2 + H_2 \rightarrow CF_3CHF_2 + HCl \qquad (2)$$

$$CF_3CHClF + H_2 \rightarrow CF_3CH_2F + HCl \qquad (3)$$

The products are hydrofluorocarbons containing no chlorine atoms, with hydrochloric acid as a by-product.

Compounds which are converted to hydrofluorocarbons by the above hydrogenation reaction include the aforementioned chloromethane, chlorodifluoromethane, chlorotrifluoromethane, chloropentafluoroethane, dichlorotetrafluoroethane, chlorotetrafluoroethane, chlorotrifluoroethane, chlorotrifluoroethylene, etc., which are normally included in pentafluoroethane in a total amount of a few thousand volppm or greater. When pentafluoroethane containing these compounds is reacted directly with fluorine gas, the methane-based compounds are converted primarily to chlorotrifluoromethane while the ethane-based compounds are converted primarily to chloropentafluoroethane, and therefore the hexafluoroethane obtained after the reaction contains chlorotrifluoromethane and chloropentafluoroethane as the major impurities.

The chloropentafluoroethane is virtually non-reactive with fluorine gas at low temperature. Investigation by the present inventors, however, has indicated that when, for example, the reaction temperature is 400° C. and the chloropentafluoroethane concentration in pentafluoroethane is no greater than about 800 vol ppm, the chloropentafluoroethane is cleaved, resulting in a chlorotrifluoromethane amount of no greater than 1 vol ppm, but when the chloropentafluoroethane concentration is greater than about 2000 vol ppm, the chlorotrifluoromethane content reaches about 2 vol ppm.

Since chlorotrifluoromethane forms an azeotropic mixture with hexafluoroethane, removal of this compound is very difficult by distillation or adsorption procedures even when the concentration is low. Consequently, it is preferred not only to remove, from the pentafluoroethane starting material, the compounds which produce chlorotrifluoromethane by reaction with fluorine gas, but also to reduce the chloropentafluoroethane content to as low a concentration as possible.

The chlorine compounds included in the pentafluoroethane used for this process are present at preferably no greater than 1 vol %, more preferably no greater than 0.5 vol % and even more preferably no greater than 0.3 vol %. If the chlorine compound content exceeds 1 vol %, the reaction temperature must be increased, possibly resulting in a shorter life of the hydrogenation catalyst.

As hydrogenation catalysts for step (1) there are preferred catalysts containing at least one element from among platinum metals such as platinum, palladium, rhodium, iridium, ruthenium and osmium, and these metals or their metal oxides or salts may be used as the starting materials. Carriers which may be used for these catalysts include active carbon, alumina and fluorinated alumina, and the element component-supporting rate is preferably at least 0.02 wt % in order to efficiently promote the intended reaction. The hydrogenation catalyst may be prepared, for example, by dissolving the metal salt in an aqueous solvent such as water, methanol or acetone, immersing the aforementioned carrier in the solution for adsorption of the necessary element, distilling off the solvent, and accomplishing heat reduction treatment with hydrogen or the like.

The reaction temperature for the hydrogenation reaction of step (1) is 150–400° C., and preferably 200–300° C. If the reaction temperature is higher than 400° C. the catalyst life will tend to be shortened, often promoting excess reaction. Excessive promotion of the hydrogenation reaction is undesirable because of production of 1,1,1-trifluoroethane, etc. Reaction control is difficult in step (2) in which the organic compound and fluorine gas participate in direct fluorination reaction, because a very large amount of reaction heat is generated and, for example, a greater reaction heat results with a larger number of C—H bonds substituted with C—F bonds in the organic compound substrate, thus tending to produce partial heat generation (hot spots). Consequently, it is preferred to use pentafluoroethane containing minimal hydrofluorocarbons (HFCs), and especially 1,1,1-trifluoroethane which contains numerous C—H bonds. On the other hand, a reaction temperature of lower than 150° C. will tend to inhibit the intended reaction.

The molar ratio of hydrogen and the mixed gas (hydrogen/chlorine compound and pentafluoroethane mixed gas) for the hydrogenation reaction of step (1) is preferably in the range of 1–20, and more preferably in the range of 2–10. The reaction pressure is preferably in a range from atmospheric pressure to 1.5 MPa. A reaction pressure exceeding 1.5 MPa can be problematic since it necessitates pressure-resistant equipment.

In this process, step (1) is carried out under the reaction conditions described above, and the reaction product will contain, along with pentafluoroethane, also hydrofluorocarbons containing no chlorine atoms, and trace amounts of unreacted chlorine compounds and acid component by-products such as hydrochloric acid, which are preferably removed.

The method of removing the acid components may be, for example, a method of contacting with a purifying agent or a method of contacting with water or an aqueous alkali solution. The gas from which the acid components have been removed is preferably dehydrated using a dehydrating agent such as zeolite and then distilled before the direct fluorination step to obtain purified pentafluoroethane, and the unreacted hydrogen is preferably separated out. Hydrogen is preferably not included in the direct fluorination reaction of step (2), because it may react violently with fluorine gas.

The chlorine compounds in the mixed gas obtained by step (1) are preferably present in a total amount of no greater than 0.05 vol %, and 1,1,1-trifluoroethane is preferably present at no greater than 0.2 vol %.

The following explanation concerns step (2) in which the gas containing the pentafluoroethane obtained by step (1) as the major component is reacted with fluorine gas.

Step (2) is carried out in the presence of a diluent gas, in order to set the concentration of the mixed gas with pentafluoroethane as the major component to below the explosive range. Specifically, the concentration of the pentafluoroethane at the reactor inlet is preferably no greater than about 6 mole percent. The diluent gas used contains at least one selected from the group consisting of tetrafluoromethane, hexafluoroethane, octafluoropropane and hydrogen fluoride, and preferably a diluent gas rich in hydrogen fluoride is used. A diluent gas rich in hydrogen fluoride is a diluent gas containing at least 50 mole percent hydrogen fluoride.

The amount of fluorine gas used may be in the range of 0.5–2.0 and preferably in the range of 0.9–1.3, in terms of the molar ratio with respect to the mixed gas containing pentafluoroethane as the major component ($F_2$/hydrogenated compound-containing pentafluoroethane). The reaction temperature is preferably 250–500° C., and more preferably 350–450° C. If the reaction temperature is higher than 500° C., the target product, hexafluoroethane, may be cleaved, producing tetrafluoromethane ($CF_4$). If the reaction temperature is below 250° C., the reaction rate may be slowed.

The method of purifying the effluent gas from step (2) is not particularly restricted, but preferably the residual unreacted fluorine gas is removed first. For example, a hydrofluorocarbon such as trifluoromethane may be added to react with and remove the excess fluorine gas. This is preferably followed by distillation, for example, distillation of the hydrogen fluoride and organic matter first. The separated hydrogen fluoride may be reused as diluent gas for the direct fluorination reaction of step (2), or it may be utilized for a different purpose.

The composition of the gas containing the separated organic matter will differ considerably depending on the diluent gas used for the reaction, and for example, when a hydrogen fluoride-rich gas or hexafluoroethane itself is used as the diluent gas, the gas obtained by the reaction will contain hexafluoroethane as the major component. When tetrafluoromethane or octafluoropropane is used as the diluent gas, purification is achieved by further distillation, but in either case, high-purity hexafluoroethane can be obtained by repeated distillation of the mixed gas which is obtained.

The distillation and purification of the mixed gas obtained by the reaction will depend on the compositional ratio, but as an example, low boiling point components such as inert gases and tetrafluoromethane are extracted from the top of a first distillation tower, and a mixed gas composed mainly of hexafluoroethane is extracted from the bottom. The mixed gas extracted from the bottom is then introduced into a second distillation tower and the low boiling point components such as inert gases and trifluoromethane are extracted from the top of the second distillation tower, after which the mixed gas composed mainly of hexafluoroethane which is extracted from the bottom is introduced into a third distillation tower and high-purity hexafluoroethane is extracted from the top of the tower, thereby accomplishing purification.

The process of the invention described above may be used to obtain hexafluoroethane with a purity of 99.9997 vol % or greater. The chlorotrifluoromethane included as an impurity is therefore less than 1 vol ppm. $CF_3CF_3$ with a purity of 99.9997 vol % or greater can be analyzed by gas chromatography (GC) methods such as TCD, FID (both including precut methods), ECD or with a gas chromatography-mass spectrometer (GC-MS).

The uses of high-purity hexafluoroethane obtained by the process of the invention will now be explained. High-purity $CF_3CF_3$, or mixed gases of high-purity $CF_3CF_3$ with inert gases such as He, $N_2$ and Ar or gases such as $O_2$ and $NF_3$ (for the purpose of the invention, these will be collectively referred to as "hexafluoroethane products") may be used as etching gases for etching steps in semiconductor device manufacturing processes or as cleaning gases for cleaning steps in semiconductor device manufacturing processes. In manufacturing processes for semiconductor devices such as LSIs and TFTs, thin-films and thick-films are formed using CVD, sputtering, vapor deposition and the like, and these are etched to form circuit patterns. The thin-film and thick-film forming apparatuses must be cleaned in order to remove unwanted accumulated matter in the apparatus inner walls, jigs, etc. Production of unwanted accumulated matter can result in particle generation, requiring constant removal in order to produce satisfactory films.

Etching methods using $CF_3CF_3$ may be carried out under various dry etching conditions such as plasma etching, microwave etching or the like, in which case the $CF_3CF_3$ may be used as a mixture with inert gases such as He, $N_2$ or Ar or gases such as HCl, $O_2$, $H_2$, $F_2$, $NF_3$ or the like in appropriate proportions.

The present invention will now be explained in greater detail by way of examples, with the understanding that the invention is in no way limited by the examples.

Pentafluoroethane Production Example 1 (Starting Material Example 1)

Tetrachloroethylene ($CCl_2$=$CCl_2$) was contacted with Molecular Sieve 4A (product of Union Showa Co., Ltd.) to remove the stabilizer and moisture in the tetrachloroethylene, and was then reacted with hydrogen fluoride (HF) in the presence of a chromium-based fluorination catalyst (first reaction: Reaction pressure of 0.4 MPa, reaction temperature of 320° C., HF/tetrachloroethylene=8 (molar ratio)). Next, the primarily dichlorotrifluoroethane ($CF_3CHCl_2$) and chlorotetrafluoroethane ($CF_3CHClF$) product obtained by the first reaction was reacted with hydrogen fluoride (second reaction: Reaction pressure of 0.45 MPa, reaction temperature of 330° C., HF/($CF_3CHCl_2$+$CF_3CHClF$)=6 (molar ratio)). After completion of the second reaction, the acid component was removed by a known method, and distillation purification was performed to obtain a distillate containing pentafluoroethane as the major component. The distillate was analyzed by gas chromatography and identified as pentafluoroethane having the composition shown in Table 1.

TABLE 1

| Compound | Purity (vol %) |
|---|---|
| $CF_3CHF_2$ | 99.7003 |
| $CH_3Cl$ | 0.0014 |
| $CHClF_2$ | 0.0009 |
| $CHF_3$ | 0.0127 |
| $CF_3CClF_2$ | 0.2819 |
| $CF_3CHClF$ | 0.0008 |
| $CF_3CCl_2F$ | 0.0009 |
| Other | 0.0011 |

Starting Material Hexafluoroethane Production Example 1 (Starting Material Example 2)

Nitrogen gas was introduced into an Inconel 600 reactor with an inner diameter of 20.6 mm and a length of 500 mm (electric heater type: passivation treated with fluorine gas at a temperature of 500° C.) through two gas inlets at a total flow rate of 30 NL/hr, and the temperature in the reactor was kept at 380° C. Next, hydrogen fluoride was introduced through the two gas inlets at a total flow rate of 50 NL/hr, and pentafluoroethane (Starting Material Example 1) obtained in Pentafluoroethane Production Example 1 was introduced through one of the gas inlets at a flow rate of 3.6 NL/hr. Fluorine gas was introduced through the other gas inlet at a flow rate of 3.9 NL/hr for fluorination reaction. The outlet gas from the reactor was contacted with an aqueous potassium hydroxide solution and an aqueous potassium iodide solution, and the hydrogen fluoride and unreacted fluorine gas in the outlet gas were removed. After contact with a dehydrating agent for drying, the dried gas was cooled and collected, and distilled for purification. The purified hexafluoroethane was analyzed by gas chromatography, giving the results shown in Table 2.

TABLE 2

| Compound | Purity (vol %) |
|---|---|
| $CF_3CF_3$ | 99.9972 |
| $CF_4$ | <0.0001 |
| $CClF_3$ | 0.0025 |
| $CF_3CHF_2$ | 0.0001 |
| Other | 0.0001 |

Catalyst Production Example 1 (Catalyst Example 1)

After placing 0.6 L of pure water in a 10 L vessel and stirring, a solution of 452 g of $Cr(NO_3)_3 \cdot 9H_2O$ and 42 g of $In(NO_3)_3 \cdot nH_2O$ (where n is approximately 5) in 1.2 L of purified water and 0.31 L of 28% aqueous ammonia water were added dropwise thereto, to a reaction solution pH in the range of 7.5–8.5 over a period of about 1 hour while controlling the flow rate of the two aqueous solutions. The obtained slurry was filtered, and the filtered solid was thoroughly washed with purified water and then dried at 120° C. for 12 hours. After pulverizing the dried solid, it was mixed with graphite and shaped into pellets using a tablet molding machine. The pellets were calcined for 4 hours under a nitrogen stream at 400° C. to prepare a catalyst precursor. The catalyst precursor was filled into an Inconel reactor and subjected to fluorination treatment (catalyst activation) under a nitrogen-diluted hydrogen fluoride stream at 350° C. and ordinary pressure. It was then subjected to fluorination treatment (catalyst activation) at 400° C. under a 100% hydrogen fluoride stream and then under a nitrogen-diluted hydrogen fluoride stream, to prepare a catalyst (Catalyst Example 1).

EXAMPLE 1

A 150 ml portion of the catalyst (Catalyst Example 1) obtained in Catalyst Production Example 1 was filled into an Inconel 600 reactor with an inner diameter of 1 inch and a length of 1 m and the temperature was kept at 280° C. while circulating nitrogen gas. Hydrogen fluoride was then supplied at 1.5 NL/hr, and starting material hexafluoroethane having the composition shown in Table 2 (Starting Material Example 2) was supplied at 3.5 NL/hr. The supply of nitrogen gas was then suspended and reaction was initiated. After 3 hours, the outlet gas from the reactor was washed with an aqueous potassium hydroxide solution to remove the acid component, and the gas composition was analyzed by gas chromatography and identified as hexafluoroethane having the composition shown in Table 3.

TABLE 3

| Compound | Purity (vol %) |
|---|---|
| $CF_3CF_3$ | 99.9972 |
| $CF_4$ | 0.0025 |
| $CClF_3$ | <0.0001 |
| $CF_3CHF_2$ | 0.0001 |
| Other | <0.0001 |

As shown in Table 3, the chlorotrifluoromethane contained in hexafluoroethane can be converted to tetrafluoromethane.

The above reaction was then carried out and the acid component-removed gas was contacted with a dehydrating agent, dried, cooled and collected, and then distilled by a known method for purification. The hexafluoroethane obtained by the distillation was analyzed by gas chromatography, giving the results shown in Table 4.

TABLE 4

| Compound | Purity |
|---|---|
| $CF_3CF_3$ | ≧99.9997 vol % |
| $CF_4$ | <0.5 vol ppm |
| $CClF_3$ | <0.5 vol ppm |
| $CF_3CHF_2$ | <0.5 vol ppm |
| Other | <1.0 vol ppm |

Based on the analysis results shown in Table 4, the purity of the hexafluoroethane was at least 99.9997 vol %, and the chlorotrifluoromethane content was less than 0.5 vol ppm. The impurities were analyzed by gas chromatography using TCD, FID, ECD and GC-MS.

EXAMPLE 2

A 100 ml portion of the catalyst (Catalyst Example 1) obtained in Catalyst Production Example 1 was filled into an Inconel 600 reactor with an inner diameter of 1 inch and a length of 1 m and the temperature was kept at 400° C. while circulating nitrogen gas. Hydrogen fluoride was then supplied at 10 NL/hr, and starting material hexafluoroethane having the composition shown in Table 2 (Starting Material Example 2) was supplied at 10 NL/hr. The supply of nitrogen gas was then suspended and reaction was initiated. After 3 hours, the outlet gas from the reactor was treated for removal of the acid component in the same manner as Example 1, and analysis was performed by gas chromatography. The results confirmed the product to be hexafluoroethane having the composition shown in Table 5.

TABLE 5

| Compound | Purity (vol %) |
|---|---|
| $CF_3CF_3$ | 99.9972 |
| $CF_4$ | 0.0026 |
| $CClF_3$ | ND |
| Other | 0.0002 |

In Table 5, ND means "not detectable" by GC-MS, i.e. a value of less than 0.1 vol ppm. The $CClF_3$ content was therefore less than 0.1 vol ppm.

The product gas dehydrated in the same manner as Example 1 was cooled and collected, and distilled under the same conditions, and the resulting hexafluoroethane was analyzed by gas chromatography, giving the results shown in Table 6.

TABLE 6

| Compound | Purity |
|---|---|
| $CF_3CF_3$ | >99.9998 vol % |
| $CF_4$ | <0.5 vol ppm |
| $CClF_3$ | <0.1 vol ppm |
| Other | <1.0 vol ppm |

As clearly shown by the analysis results in Table 6, the $CClF_3$ content was less than 0.1 vol ppm, and therefore high-purity hexafluoroethane had been obtained.

Pentafluoroethane Production Example 2 (Starting Material Example 3)

Tetrachloroethylene ($CCl_2$=$CCl_2$) was contacted with Molecular Sieve 4A (product of Union Showa K. K.) to remove the stabilizer and moisture in the tetrachloroethylene, and was then reacted with hydrogen fluoride (HF) in the presence of a chromium-based fluorination catalyst (first reaction: Reaction pressure of 0.4 MPa, reaction temperature of 300° C., HF/tetrachloroethylene=8 (molar ratio)). Next, the mixed gas containing primarily dichlorotrifluoroethane ($CF_3CHCl_2$) and chlorotetrafluoroethane ($CF_3CHClF$) obtained by the first reaction was reacted with hydrogen fluoride (second reaction: Reaction pressure of 0.4 MPa, reaction temperature of 330° C., HF/($CF_3CHCl_2$+$CF_3CHClF$)=6 (molar ratio)). After completion of the second reaction, the acid component was removed by a known method, and distillation purification was performed to obtain a distillate containing mostly pentafluoroethane as the major component. The distillate was analyzed by gas chromatography and identified as a mixed gas having the composition shown in Table 7 (Starting Material Example 3).

TABLE 7

| Compound | Purity (vol %) |
|---|---|
| $CF_3CHF_2$ | 99.4290 |
| $CH_3Cl$ | 0.0011 |
| $CHClF_2$ | 0.0008 |
| $CHF_3$ | 0.0218 |

TABLE 7-continued

| Compound | Purity (vol %) |
|---|---|
| $CClF_3$ | 0.0006 |
| $CF_3CClF_2$ | 0.5439 |
| $CF_3CHClF$ | 0.0007 |
| $CF_3CCl_2F$ | 0.0011 |
| $CF_3CH_2Cl$ | 0.0003 |
| Other | 0.0007 |

Pentafluoroethane Production Example 3 (Starting Material Example 4)

The mixed gas containing pentafluoroethane as the major component which was obtained by the process described above (Starting Material Example 3) was distilled by a known method. The distillate was analyzed by gas chromatography and identified as a mixed gas having the composition shown in Table 8 (Starting Material Example 4).

TABLE 8

| Compound | Purity (vol %) |
|---|---|
| $CF_3CHF_2$ | 99.7984 |
| $CHClF_2$ | 0.0003 |
| $CHF_3$ | 0.0024 |
| $CF_3CClF_2$ | 0.1989 |

Catalyst Production Example 2 (Catalyst Example 2)

Sodium palladium chloride was dissolved in water, and a 1.6 mmφ spherical alumina support was immersed therein for adsorption of the palladium salt, after which the solvent was distilled off at a temperature of 100° C., calcining was conducted in air at 300° C., and hydrogen reduction was accomplished at 350° C. The supporting rate of the obtained palladium catalyst was 2.0%.

Catalyst Production Example 3 (Catalyst Example 3)

Platinic chloride was dissolved in water, and a 1.6 mmφ spherical alumina support was immersed therein for adsorption of the platinum salt, after which the solvent was distilled off at a temperature of 100° C., calcining was conducted in air at 300° C., and hydrogen reduction was accomplished at 350° C. The supporting rate of the obtained platinum catalyst was 2.0%.

EXAMPLE 3

A 100 ml portion of the catalyst (Catalyst Example 2) obtained in Catalyst Production Example 2 was filled into an Inconel 600 reactor with an inner diameter of 1 inch and a length of 1 m and the temperature was kept at 280° C. while circulating nitrogen gas. Hydrogen was then supplied at a flow rate of 0.36 NL/hr, the mixed gas having the composition shown in Table 7 (Starting Material Example 3) was supplied at 8.33 NL/hr, and then the supply of nitrogen gas was suspended and a reaction (step (1)) was initiated. After 2 hours, the outlet gas from the reactor was washed with an aqueous solution of potassium hydroxide for removal of the acid component, and then analysis of the gas composition by gas chromatography identified it as a mixed gas composed mainly of pentafluoroethane having the composition shown in Table 9.

TABLE 9

| Compound | Purity (vol %) |
|---|---|
| $CF_3CHF_2$ | 99.9177 |
| $CH_4$ | 0.0013 |
| $CH_2F_2$ | 0.0009 |
| $CHF_3$ | 0.0226 |
| $CF_3CH_2F$ | 0.0126 |
| $CF_3CH_3$ | 0.0386 |
| $CF_3CClF_2$ | 0.0058 |
| Other | 0.0005 |

The mixed gas composed mainly of pentafluoroethane having the composition shown in Table 9, which was obtained by the process described above, was distilled by a known method, and after removing the low boiling point components such as the inert gas and hydrogen gas, a direct fluorination reaction (step (2)) was conducted with fluorine gas.

Nitrogen gas was introduced into an Inconel 600 reactor with an inner diameter of 20.6 mmφ and a length of 500 mm (electric heater type reactor: passivation treated with fluorine gas at a temperature of 500° C.) through two gas inlets at a total flow rate of 30 NL/hr, and the temperature in the reactor was kept at 420° C. Next, hydrogen fluoride was introduced through the two gas inlets at a total flow rate of 50 NL/hr, and the above-mentioned mixed gas composed mainly of pentafluoroethane from which the low boiling point components had been removed was introduced through one of the gas inlets at a flow rate of 3.5 NL/hr. Fluorine gas was introduced through the other gas inlet at a flow rate of 3.85 NL/hr and reacted therewith. After 3 hours, the outlet gas from the reactor was contacted with an aqueous potassium hydroxide solution and an aqueous potassium iodide solution, and the hydrogen fluoride and unreacted fluorine gas were removed. After contact with a dehydrating agent for drying, the dried gas composition was analyzed by gas chromatography. The analysis results are shown in Table 10.

TABLE 10

| Compound | Purity (vol %) |
|---|---|
| $CF_3CF_3$ | 99.9541 |
| $CF_4$ | 0.0388 |
| $CHF_3$ | 0.0012 |
| $CF_3CHF_2$ | <0.0001 |
| $CF_3CH_2F$ | trace |
| $CF_3CClF_2$ | 0.0058 |

The dried gas composed mainly of hexafluoroethane was cooled and collected, and purified by distillation. The purified gas was analyzed by gas chromatography using TCD, FID, ECD and GC-MS, and the results shown in Table 11 were obtained.

TABLE 11

| Compound | Purity vol ppm |
|---|---|
| $CF_3CHF_2$ | <0.5 vol ppm |
| $CF_3CH_2F$ | <0.5 vol ppm |
| $CF_4$ | <0.4 vol ppm |
| $SF_6$ | <0.4 vol ppm |
| $CF_3CClF_2$ | <0.1 vol ppm |
| $CF_3CF_3$ | >99.9998 vol % |

As clearly seen by the analysis results in Table 11, the hexafluoroethane contained virtually no impurities, thus demonstrating that high-purity hexafluoroethane had been obtained, with a purity of at least 99.9997 vol %.

EXAMPLE 4

A reaction (step (1)) was carried out with the same conditions and procedure as Example 3, except that 100 ml of catalyst (Catalyst Example 3) was filled in and the mixed gas of Starting Material Example 4 was used. The reactor outlet gas was treated in the same manner and then analyzed, giving the results shown in Table 12.

TABLE 12

| Compound | Purity (vol %) |
| --- | --- |
| $CF_3CHF_2$ | 99.9692 |
| $CH_4$ | 0.0002 |
| $CH_2F_2$ | 0.0002 |
| $CF_3CH_2F$ | 0.0056 |
| $CF_3CH_3$ | 0.0215 |
| $CF_3CClF_2$ | 0.0012 |
| $CHF_3$ | 0.0021 |

The mixed gas composed mainly of pentafluoroethane having the composition shown in Table 12, which was obtained by the process described above, was distilled by a known method, and after removing the low boiling point components such as the inert gas and hydrogen gas, a direct fluorination reaction (step (2)) was conducted with fluorine gas using the same conditions and procedure as Example 3. The gas obtained by treating the reactor outlet gas according to the same process as Example 3 was analyzed by gas chromatography, giving the results shown in Table 13.

TABLE 13

| Compound | Purity (vol %) |
| --- | --- |
| $CF_3CF_3$ | 99.9680 |
| $CF_4$ | 0.0314 |
| $CHF_3$ | 0.0002 |
| $CF_3CHF_2$ | <0.0001 |
| $CF_3CH_2F$ | <0.0001 |
| $CF_3CH_3$ | <0.0001 |
| $CF_3CClF_2$ | <0.0001 |

The mixed gas composed mainly of hexafluoroethane was cooled and collected, and then purified by distillation. Analysis of the purified gas indicated a hexafluoroethane purity of at least 99.9998 vol %, a chlorine compound impurity content of less than 1 vol ppm, and a starting material pentafluoroethane content of less than 1 vol ppm.

COMPARATIVE EXAMPLE 1

A reaction (step (1)) was conducted using the same conditions and procedure as Example 3, except for a reaction temperature of 430° C., and the product was analyzed. The results are shown in Table 14.

TABLE 14

| Compound | Purity (vol %) |
| --- | --- |
| $CF_3CHF_2$ | 99.5373 |
| $CH_4$ | 0.0134 |
| $C_2H_6$ | 0.0098 |
| $CH_2F_2$ | 0.0002 |
| $CHF_3$ | 0.0189 |
| $CF_3CH_2F$ | 0.0043 |

TABLE 14-continued

| Compound | Purity (vol %) |
| --- | --- |
| $CF_3CH_3$ | 0.4150 |
| $CF_3CClF_2$ | 0.0044 |
| Other | 0.0011 |

As clearly seen from the analysis results in Table 14, when step (1) was conducted at a reaction temperature of higher than 400° C., excess hydrogenation reaction was promoted, thereby notably increasing the amount of 1,1,1-trifluoroethane product. Methane and ethane were also produced, and deterioration of the catalyst was observed.

COMPARATIVE EXAMPLE 2

A reaction (step (1)) was conducted with the same conditions and procedure as Example 3, except for a reaction temperature of 130° C., and the product was analyzed. When step (1) was conducted at a reaction temperature of lower than 150° C., hydrogenation reaction of the chlorine compounds was almost completely inhibited, resulting in a chloropentafluoroethane conversion rate of about 19%.

COMPARATIVE EXAMPLE 3

A direct fluorination reaction (step (2)) was conducted using the same conditions and procedure as Example 3, except for using the mixed gas of Starting Material Example 3, and after removing the hydrogen fluoride and unreacted fluorine gas contained in the reactor outlet gas, analysis was performed by gas chromatography. The results are shown in Table 15.

TABLE 15

| Compound | Purity (vol %) |
| --- | --- |
| $CF_3CF_3$ | 99.4210 |
| $CF_4$ | 0.0308 |
| $CClF_3$ | 0.0046 |
| $CF_3CHF_2$ | 0.0002 |
| $CF_3CClF_2$ | 0.5419 |
| $CF_3CCl_2F$ | 0.0009 |
| Other | 0.0006 |

As clearly seen in Table 15, direct fluorination reaction using pentafluoroethane with a high chlorine compound content produced chlorotrifluoromethane, which is difficult to separate.

INDUSTRIAL APPLICABILITY

According to the procedure of the present invention, it is possible to obtain high-purity $CF_3CF_3$ and the obtained $CF_3CF_3$ is suitable for use as an etching gas or cleaning gas for semiconductor device manufacturing steps.

The invention claimed is:

1. A process for production of hexafluoroethane which comprises a step (1) in which pentafluoroethane containing chlorine compounds with 1–3 carbon atoms is reacted with hydrogen in a gas phase in the presence of a hydrogenation catalyst at 150–400° C. for hydrogenation of said chlorine compounds to obtain a crude pentafluoroethane, and a step (2) in which the product of step (1) is reacted with fluorine in a gas phase in the presence of a diluent gas to produce hexafluoroethane, wherein the product of step (1) used in step (2) is purified pentafluoroethane obtained by distillation of the crude pentafluoroethane, wherein unreacted hydrogen is removed by said distillation, wherein said chlorine compounds included in the chlorine compound-containing pentafluoroethane used in step (1) are present at no greater than 1 vol %, and wherein said chlorine compound-containing pentafluoroethane used in step (1) contains pentafluoroethane in an amount of at least 99 vol %.

2. A process according to claim 1, which comprises a further step in which the product obtained in step (2) is distilled to purify the hexafluoroethane.

3. A process according to claim 1 or 2, which comprises a further step in which hydrochloric acid is removed from the reaction product obtained in step (1).

4. A process according to claim 1 or 2, wherein said chlorine compounds are one or more compounds selected from the group consisting of chloromethane, chlorotrifluoromethane, chloropentafluoroethane, dichlorotetrafluoroethane, chlorotetrafluoroethane, chlorotrifluoroethane and chlorotrifluoroethylene.

5. A process according to claim 1, wherein said chlorine compounds included in the chlorine compound-containing pentafluoroethane used in step (1) are present at no greater than 0.5 vol %.

6. A process according to claim 1 or 2, wherein the hydrogenation catalyst of step (1) contains at least one element selected from platinum metals.

7. A process according to claim 6, wherein the hydrogenation catalyst of step (1) is a catalyst having at least one element selected from platinum metals supported on at least one support selected from the group consisting of active carbon, alumina and fluorinated alumina.

8. A process according to claim 1 or 2, wherein the amount of hydrogen used in step (1) is in a molar ratio of 1–20 with respect to the chlorine compound-containing pentafluoroethane.

9. A process according to claim 1 or 2, wherein the trifluoroethane is included in an amount of no greater than 0.2 vol % in the product of step (1) used for step (2).

10. A process for production of hexafluoroethane according to claim 1 or 2, wherein the chlorine compounds with 1–3 carbon atoms are included in an amount of no greater than 0.05 vol % in the product of step (1) used for step (2).

11. A process according to claim 1 or 2, wherein the diluent gas of step (2) is a gas containing at least one selected from the group consisting of tetrafluoromethane, hexafluoroethane, octafluoropropane and hydrogen fluoride.

12. A process according to claim 11, wherein the diluent gas of step (2) is a hydrogen fluoride-rich gas.

13. A process according to claim 1 or 2, wherein the reaction temperature in step (2) is 250–500° C.

14. A process according to claim 13, wherein the reaction temperature in step (2) is 350–450° C.

15. A process according to claim 1 or 2, wherein the chlorine compound-containing pentafluoroethane used in step (1) is a gas composed mainly of pentafluoroethane obtained by reacting tetrachloroethylene or its fluorinated product with hydrogen fluoride.

16. A process according to claim 15, wherein the gas composed mainly of pentafluoroethane is a gas obtained by distillation of a gas obtained by reacting tetrachloroethylene or its fluorinated product with hydrogen fluoride.

* * * * *